United States Patent
Simon Soria

(10) Patent No.: US 10,427,121 B2
(45) Date of Patent: Oct. 1, 2019

(54) NON INTRUSIVE AGITATION SYSTEM

(71) Applicant: ASOCIACION CENTRO DE INVESTIGACION COOPERATIVA EN BIOMATERIALES (CIC biomaGUNE), San Sebastian (ES)

(72) Inventor: Marcos Simon Soria, San Sebastian (ES)

(73) Assignee: ASOCIACION CENTRO DE INVESTIGACION COOPERATIVA EN BIOMATERIALES (CIC biomaGUNE), San Sebastion (ES)

( * ) Notice: Subject to any disclaimer, the term of this patent is extended or adjusted under 35 U.S.C. 154(b) by 320 days.

(21) Appl. No.: 14/765,252

(22) PCT Filed: Feb. 1, 2013

(86) PCT No.: PCT/EP2013/052039
§ 371 (c)(1),
(2) Date: Jul. 31, 2015

(87) PCT Pub. No.: WO2014/117859
PCT Pub. Date: Aug. 7, 2014

(65) Prior Publication Data
US 2015/0367303 A1 Dec. 24, 2015

(51) Int. Cl.
*B01F 7/00* (2006.01)
*B01F 7/08* (2006.01)
(Continued)

(52) U.S. Cl.
CPC ...... *B01F 15/0085* (2013.01); *B01F 7/00725* (2013.01); *B01F 7/086* (2013.01);
(Continued)

(58) Field of Classification Search
CPC .... C12M 23/26; C12M 27/06; C12M 227/06; B01F 7/1695; B01F 11/0042;
(Continued)

(56) References Cited

U.S. PATENT DOCUMENTS 2,124,983 A * 7/1938 Martin ............... B03B 5/16
209/455
2,203,479 A * 6/1940 Witwer ............... D06F 19/00
134/196
(Continued)

FOREIGN PATENT DOCUMENTS

DE 44 26 421 A1 2/1996
SU 1560427 A1 4/1990

OTHER PUBLICATIONS

English automatic translation of correseponding document of Germany 44 26 421 A1, (Feb. 1, 1996) 10 pages, no date of translation.
(Continued)

*Primary Examiner* — Tony G Soohoo
(74) *Attorney, Agent, or Firm* — Oblon, McClelland, Maier & Neustadt, L.L.P.

(57) ABSTRACT

A device for non intrusive agitation of a fluid is provided, including a container adapted to contain the fluid, at least one of the walls thereof includes a membrane and a main movable stirring means inside the container adapted to stir at least the fluid. The first flexible element is adapted to interfere mechanically with an external movable impulsion means, thus creating a deformation which has a mechanical interference with the main movable stirring means. This movement of such impulsion means is transmitted to the main movable stirring means by the interposition of the first flexible element.

25 Claims, 5 Drawing Sheets

(51) Int. Cl.
| | |
|---|---|
| *B01F 7/16* | (2006.01) |
| *B01F 11/00* | (2006.01) |
| *B01F 15/00* | (2006.01) |
| *C12M 1/00* | (2006.01) |
| *C12M 1/06* | (2006.01) |
| *F16D 1/076* | (2006.01) |

(52) U.S. Cl.
CPC ........ *B01F 7/1695* (2013.01); *B01F 11/0045* (2013.01); *B01F 15/00396* (2013.01); *B01F 15/00487* (2013.01); *C12M 23/26* (2013.01); *C12M 27/06* (2013.01); *B01F 11/0042* (2013.01); *B01F 2015/00649* (2013.01); *B01F 2215/0073* (2013.01)

(58) Field of Classification Search
CPC ............ B01F 11/0045; B01F 15/00396; B01F 15/00487; B01F 15/0085; B01F 2015/00649; B01F 2215/0073; B01F 7/00725; B01F 7/086
See application file for complete search history.

(56) References Cited

U.S. PATENT DOCUMENTS

| | | | | | |
|---|---|---|---|---|---|
| 2,466,327 | A | * | 4/1949 | Rieber | G04F 3/00 188/268 |
| 2,499,203 | A | * | 2/1950 | Warren | B01F 11/0071 366/275 |
| 3,063,683 | A | * | 11/1962 | Westbrook | B01F 11/0042 222/214 |
| 3,132,848 | A | * | 5/1964 | Garlinghouse | B01F 11/0045 298/11 |
| 3,290,017 | A | | 12/1966 | Davies, et al. | |
| 3,313,240 | A | * | 4/1967 | Bentov | D21F 1/00 137/268 |
| 3,489,393 | A | * | 1/1970 | Waraksa | B01F 11/0042 356/39 |
| 3,588,054 | A | * | 6/1971 | Ljungberg et al. | B01F 11/0042 366/150.1 |
| 3,595,530 | A | * | 7/1971 | Hubers | B01F 5/0685 366/332 |
| 3,656,716 | A | * | 4/1972 | Ljungerg | B01F 11/0042 366/150.1 |
| 3,712,591 | A | * | 1/1973 | Booth | B01F 5/0685 366/275 |
| 3,740,028 | A | * | 6/1973 | Bodine | B01F 11/0045 366/114 |
| 3,765,127 | A | * | 10/1973 | Garlinghouse | B24B 31/10 366/185 |
| 3,833,203 | A | * | 9/1974 | Garlinghouse | B01F 11/0045 366/113 |
| 3,962,892 | A | * | 6/1976 | Garlinghouse | B01F 11/0045 134/118 |
| 4,095,288 | A | * | 6/1978 | Garlinghouse | B01F 11/0045 366/219 |
| 4,207,007 | A | * | 6/1980 | Yamshikov | A23N 12/023 366/275 |
| 4,685,811 | A | * | 8/1987 | Pollard | B01F 11/0045 366/275 |
| 5,188,455 | A | * | 2/1993 | Hammerstedt | B01F 11/0042 137/896 |
| 5,240,323 | A | * | 8/1993 | Haber | B01F 11/0045 206/219 |
| 5,628,562 | A | * | 5/1997 | Krumm | B01F 11/0042 366/240 |
| 5,826,979 | A | * | 10/1998 | Foss | B01F 7/16 366/242 |
| 6,190,913 | B1 | * | 2/2001 | Singh | B01F 11/0017 435/383 |
| 6,491,422 | B1 | * | 12/2002 | Rutten | B01F 11/0258 366/116 |
| 7,278,780 | B2 | * | 10/2007 | Goodwin | B01F 13/0818 366/273 |
| 7,541,178 | B2 | * | 6/2009 | Takagi | C12M 23/14 366/275 |
| 7,972,058 | B2 | * | 7/2011 | Furey | B01F 11/0071 366/275 |
| 8,366,311 | B2 | * | 2/2013 | Vanhamel | B01F 7/001 366/102 |
| 8,491,178 | B2 | * | 7/2013 | Breidenthal | B01F 11/0045 366/142 |
| 8,794,821 | B2 | * | 8/2014 | Watkins | B01F 7/00675 366/276 |
| 8,870,443 | B2 | * | 10/2014 | Greller | B01F 7/00633 366/102 |
| 9,744,506 | B2 | * | 8/2017 | Fan | B01F 11/00 |
| 2004/0047232 | A1 | * | 3/2004 | Terentiev | B01F 7/00908 366/273 |
| 2004/0062140 | A1 | * | 4/2004 | Cadogan | B01F 7/18 366/144 |
| 2005/0078552 | A1 | * | 4/2005 | Zambaux | B01F 7/1695 366/241 |
| 2005/0206260 | A1 | * | 9/2005 | Akiyama | C30B 15/30 310/104 |
| 2005/0249033 | A1 | * | 11/2005 | Krause | B01F 11/0082 366/332 |
| 2006/0013063 | A1 | * | 1/2006 | Singh | B01F 11/0017 366/239 |
| 2006/0140052 | A1 | * | 6/2006 | Esveld | B01F 11/0045 366/275 |
| 2007/0102450 | A1 | * | 5/2007 | Stiers | B01F 11/04 222/181.1 |
| 2007/0140047 | A1 | * | 6/2007 | Ray | B01F 11/0065 366/197 |
| 2007/0253287 | A1 | * | 11/2007 | Myhrberg | B01F 7/162 366/273 |
| 2007/0253288 | A1 | * | 11/2007 | Mennenga | B01F 11/0082 366/274 |
| 2009/0275121 | A1 | * | 11/2009 | Greller | B01F 3/04262 435/295.1 |
| 2009/0314666 | A1 | * | 12/2009 | Reif | B01F 15/0085 206/221 |
| 2010/0015696 | A1 | * | 1/2010 | Claes | B01F 3/04269 435/303.3 |
| 2010/0301042 | A1 | * | 12/2010 | Kahlert | B01F 7/18 220/23.86 |
| 2011/0013473 | A1 | * | 1/2011 | Ludwig | B01F 3/04269 366/101 |
| 2011/0044567 | A1 | * | 2/2011 | Barbaroux | B01F 7/163 383/120 |
| 2011/0058448 | A1 | * | 3/2011 | Reif | B01F 7/16 366/250 |
| 2011/0158037 | A1 | * | 6/2011 | Bernard | B01F 3/1207 366/173.2 |
| 2012/0003733 | A1 | * | 1/2012 | Gueneron | C12M 23/26 435/289.1 |
| 2012/0027324 | A1 | * | 2/2012 | Morrissey | B01F 7/162 383/105 |
| 2015/0367303 | A1 | * | 12/2015 | Simon Soria | B01F 7/00725 366/145 |
| 2016/0106624 | A1 | * | 4/2016 | Camisani | A61M 1/025 435/325 |
| 2016/0375416 | A1 | * | 12/2016 | Ruberg | B01F 15/0278 366/184 |

OTHER PUBLICATIONS

International Search Report dated Oct. 22, 2013, in PCT/EP2013/052039, filed Feb. 1, 2013.

* cited by examiner

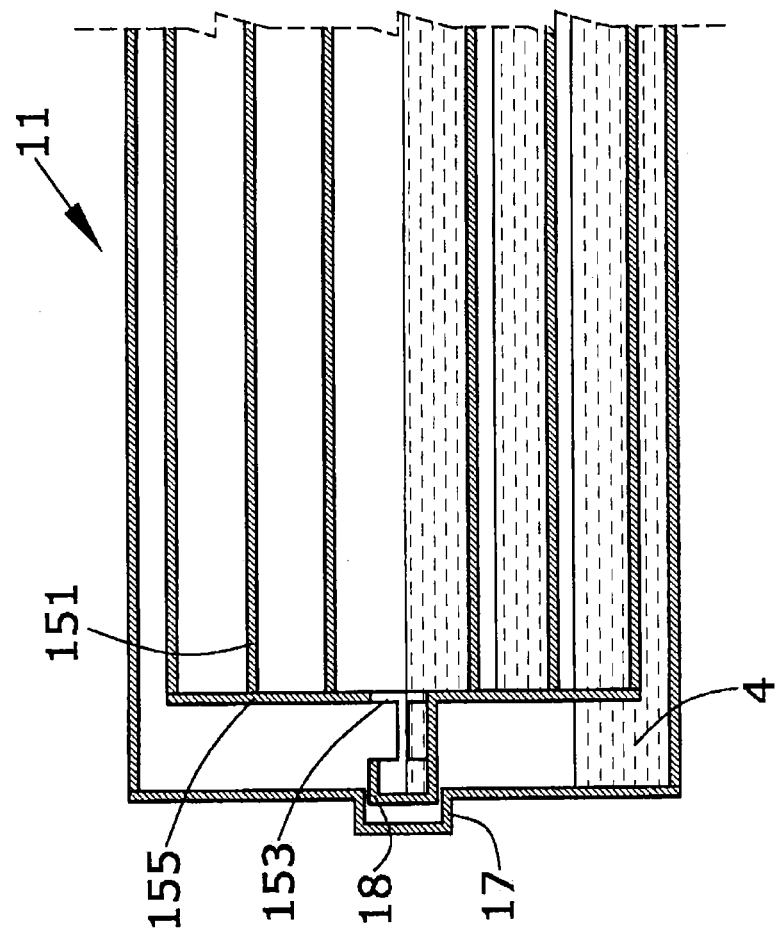
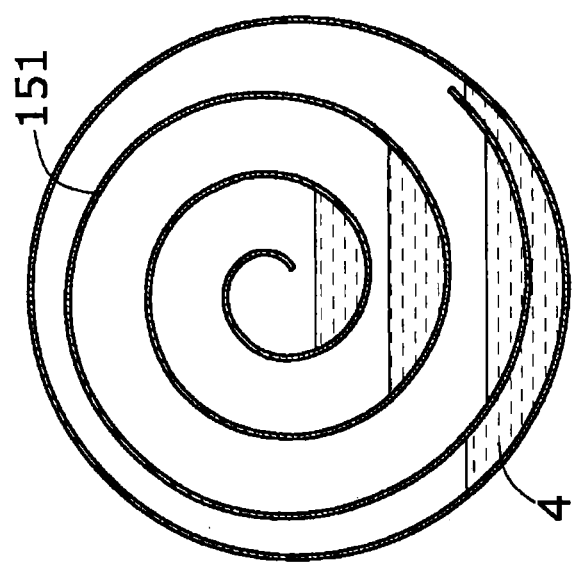
FIG. 3B
FIG. 3A

NON INTRUSIVE AGITATION SYSTEM

FIELD OF THE INVENTION

The invention provides means for the controlled, contained and non-intrusive agitation of the contents of a closed container, without introducing any piece, or particle inside said container.

BACKGROUND OF THE INVENTION

Some processes, such as cell culture, need that a fluid inside a container is agitated. This step can be achieved in many ways, but achieving it by introducing some moving external piece inside the container has many disadvantages.

Firstly, it is more difficult to ensure the watertightness of the container, as there must be an opening for the external piece to come in, and that opening must let the piece move. Furthermore, it is more difficult to ensure the sterility of the inner part of the container.

Different solutions have been proposed to achieve contained, non-intrusive agitation within closed vessels. These solutions can be grouped into three broad approaches:

Agitation of the Vessel.

U.S. Pat. No. 6,190,913 describes a rocking platform that applies a rocking movement to a bag partially filled with a cell suspension, thus achieving simultaneous agitation of the suspension and aeration of the culture due to gas exchange between the liquid phase and the gas phase on top.

U.S. Pat. No. 3,941,661 describes adherent cells growing on the inner wall of a cylindrical bottle which are periodically submerged in a liquid culture medium contained in the bottle as the horizontal bottle rotates about its longitudinal axis.

U.S. Pat. No. 5,816,702 proposes the use of a vane mounted in the interior of a drum thus increasing the mixing of the fluid contents of the vessel.

U.S. Pat. No. 4,732,487 describes the application of an oscillating movement to the wall of a vessel such that this movement transfers the oscillating movement to a mixing plate secured to the inner side of the oscillating wall. The plate oscillates at larger amplitude than that applied to the wall, thus producing a mixing effect of liquids contained in the vessel.

U.S. Pat. No. 4,685,811 describes the use of a fluidic diode comprising a perforated plate contained in a vessel in such a way that the different path followed by the liquid when flowing in different directions creates a mixing effect.

U.S. Pat. No. 7,083,323 proposes the movement from one compartment to another of the liquid content of a multi-compartment flexible vessel. By, compressing the walls of the different compartments, the liquid is forced to pass through small passages that increase flow speed and create a mixing effect.

Bubbling Gas

U.S. Pat. No. 5,443,985 proposes the culture of cells in suspension using a long inclined culture chamber where gas bubbles introduced at the bottom of the chamber progressed to the top of the chamber along the interphase between the cell suspension and the chamber wall, thus gently agitating the cell suspension contained in the chamber and simultaneously providing gas exchange.

Magnetic Agitation

Magnetic coupling is commonly used in open systems to agitate the liquid contents of vessels. In these systems an open vessel containing the liquid to be agitated and a magnet Is placed on top of a surface that covers a rotating magnetic field. Examples of this technique can be found in U.S. Pat. No. 4,209,259 or in U.S. Pat. No. 3,647,632.

Document U.S. Pat. No.3,290,017 A describes a partitioned container for storing a plurality of different ingredients that must be kept separated until ready for use. In one of the embodiments, fingers are used to push a ball-shaped barrier along the inside of a tube.

However, all of these existing systems have at least one of the following drawbacks: the agitation intensity, and therefore the shear forces, is poorly controlled, thus limiting the application to shear resistant contents; continuous fluid feeding and exhausting is not possible due to tubing entanglement, limiting automation; direct agitation occurs only in a reduced volume of the vessel content, reducing efficacy; liquid transfer from one vessel to another through small passages is required to achieve agitation, therefore limiting the size of solid structures in the interior of the vessel and increasing the size of the overall system ; the use of metallic components in the interior of the vessel prevents the use of some sterilizing technologies, what prevents the use of pre-sterilized vessels; and the agitating mechanism is large and complex, limiting its application in particularly controlled environments.

All of the afore-mentioned drawbacks are overcome by the disclosed invention.

SUMMARY OF THE INVENTION

The invention suggests an improved solution to the previous drawbacks. The invention relates to a first interrelated product according to claim 1. Preferred embodiments of the invention are defined in dependent claims.

In a first inventive aspect, the invention provides a first inter-related product for non intrusive agitation of a fluid, suitable for cell culture, provided in the form of a device comprising:

a container adapted to contain directly or by a further second container the fluid wherein at least one of the walls of the container comprises a first flexible element, preferably a membrane, having an internal surface oriented towards the inner part of the container and an external surface oriented towards the outer part of the container, main movable stirring means located inside the container adapted to stir at least the fluid, wherein, the external surface of the first flexible element Is adapted to interfere mechanically with an external movable impulsion means thus creating a deformation on the internal surface of the first flexible element, such that said deformation of the internal surface of the first flexible element has a mechanical interference with the main movable stirring means, and the movement of such impulsion means is transmitted to the main movable stirring means by the interposition of the first flexible element.

In a preferred embodiment, the main movable stirring means comprise first protrusions.

In a preferred embodiment the first protrusions, or at least one of the first protrusions, are cylindrical protrusions, semicylindrical protrusions, semispherical protrusions, idle cylinders, idle spherical elements, retractile bars, or a combination of them.

In a preferred embodiment, the main movable stirring means are mechanically coupled to secondary stirring means located within the container wherein the movement of the secondary stirring means is driven by the movement of the main movable stirring means.

In a preferred embodiment, the main movable stirring means and the secondary stirring means are two coupled gear wheel shaped elements, fitted to the walls of the container so that when rotating, the first inter-related product works as an impeller, pumping fluid from a fluid supply to a fluid drain.

In a preferred embodiment, the surface of the main movable stirring means is modified by means of functionalising said surface or coating said surface with catalysts, chemical reagents, cells, polymers or crystals.

In a preferred embodiment, the first inter-related product further comprises inlet and outlet means to supply and extract at least one fluid from the container.

In a preferred embodiment, the container comprises a guiding housing and the main movable stirring means comprise at least one corresponding guided projection adapted to be housed in the guiding housing of the container allowing a guided movement of the main movable stirring means in respect of the container.

In a preferred embodiment, the container comprises thermostating means adapted to keep a constant temperature within the container.

In a preferred embodiment,
the container is a cylindrical wall extended according to a longitudinal axis and limited by two ends wherein at least one end is a transversal wall comprising the first flexible element,
the container is adapted to be oriented such that the longitudinal axis is essentially perpendicular to the direction of gravity, and
the main movable stirring means comprise a plate and a driven structure attached thereto adapted to interact with the deformation of the internal surface of the first flexible element.

The term cylindrical must be interpreted in its broadest sense, i.e., a surface generated by a closed curve or generatrix extending according to a directrix, for instance a longitudinal axis or a curve of low curvature. For instance, examples of cylindrical walls are those offered by tubular bodies having a circular or polygonal section.

In a preferred embodiment, the plate comprises a spiral section and extends along the longitudinal axis of the container between a first end and a second end.

In a preferred embodiment, the spiral section is transversal to the longitudinal axis of the container.

In a preferred embodiment, the spiral section comprised in the plate is closed in both ends by two lateral walls, at least one of the walls having a drain hole in communication with the internal cavity of the container for allowing the outlet of a fluid from the inner part of the plate comprising the spiral section such that, in an operative mode, the plate with the spiral section is adapted to transport, rotation the fluid of the container to the inner part of the plate comprising the spiral section, and the drain hole is adapted to return the fluid from the inner part of the plate to the outer part of the plate back to be in contact with the inner walls of the container.

In a preferred embodiment, the main movable stirring means comprise a set of nested cylinders such that:
each cylinder is in fluid connection with the cylinder immediately housing it,
the drain hole of the plate having the spiral section is in fluid communication with the most inner cylinder, and
the outermost cylinder is in fluid communication with the container;
such that the outlet of the fluid from the inner part of the plate having the spiral section to the container is by the interposition of the set of nested cylinders.

In a preferred embodiment, the fluid connection of each cylinder with the cylinder immediately housing it is by means of outlets located in alternating ends in such a way that the flow alternates the direction when flowing in each cylinder.

In a preferred embodiment,
the container is a cylindrical wall extended according to a longitudinal axis and limited by two ends wherein the cylindrical wall comprises the first flexible element,
the container is adapted to be oriented such that the longitudinal axis is essentially parallel to the direction of gravity, and
the main movable stirring means comprise a driven structure attached thereto adapted to interact with the deformation of the internal surface of the first flexible element.

In a preferred embodiment, the first protrusions are cylindrical first protrusions substantially parallel to the longitudinal axis of the container and linked with the driven structure by connecting elements.

In a preferred embodiment, the main movable stirring means comprise also a plate comprising a helical portion or helical blades with the longitudinal axis of the helix essentially parallel to the longitudinal axis of the container and adapted to raise the fluid contained in the container.

In a preferred embodiment, the container comprises a second container to store said fluid and the second container is integral with the main movable stirring means.

In a second inventive aspect, the invention provides a second inter-related product provided in the form of impulsion means adapted to act over the surface of a flexible element, particularly the external surface of the first flexible element of the first inter-related product according to the first inventive aspect and intended to be located outside the container of such first inter-related product, wherein said impulsion means comprise at least one second protrusion adapted to interfere mechanically with the external surface of the flexible element causing the deformation of said flexible element protruding the internal surface.

In a preferred embodiment, the second inter-related product is further adapted to move in a lineal trajectory or in a circular trajectory or in a combination of both.

In a preferred embodiment, the second inter-related product adapted to, act over a first inter-related product according to the first inventive aspect, further comprises a plurality of second protrusions, and the impulsion means and the main movable stirring means are arranged so that the second protrusions are suitable for housing the first protrusions by the interposition of the first flexible element.

In a preferred embodiment, the second protrusions are adapted to house the first protrusions in more than one housing position.

In a preferred embodiment, at least one of the second protrusions are cylindrical protrusions, semicylindrical protrusions, semispherical protrusions, idle cylinders, idle spherical elements, or a combination of them.

In a preferred embodiment, the second inter-related product is adapted to act over a device according to a preferred embodiment of a first inter-related product according to the first inventive aspect, the second protrusions being one or more cylinders parallel to the longitudinal axis of the container.

In a preferred embodiment, the one or more cylinders parallel to the longitudinal axis of the container are adapted to be rotatable around the first flexible peripheral wall and their longitudinal axis in order to reduce the shear forces in respect of the first flexible element.

In a third inventive aspect, the invention provides a system comprising a combination of a first inter-related product according to the first inventive aspect and a second inter-related product according to the second inventive aspect.

In a preferred embodiment, the first inter-related product is located in a first chamber and the second inter-related product is located in a second chamber, said chambers separated by a wall, the wall further comprising a second flexible element located between the impulsion means and the first flexible element of the container, preferably a membrane, to provide a separation between the environment surrounding the first inter-related product and the environment surrounding the second inter-related product.

All the features described in this specification (including the claims, description and drawings) and/or all the steps of the described method can be combined in any combination, with the exception of combinations of such mutually exclusive features and/or steps.

BRIEF DESCRIPTION OF THE DRAWINGS

These and other characteristics and advantages of the invention will be more clearly highlighted from the following detailed description of preferred realization forms, given only as illustrative, not limitative examples, referred to the annexed figures.

FIGS. 3A-3B Represent details of the interaction between the fluid and the spiral plate in the embodiment shown in FIG. 1.

DETAILED DESCRIPTION OF THE INVENTION

Figure 1:
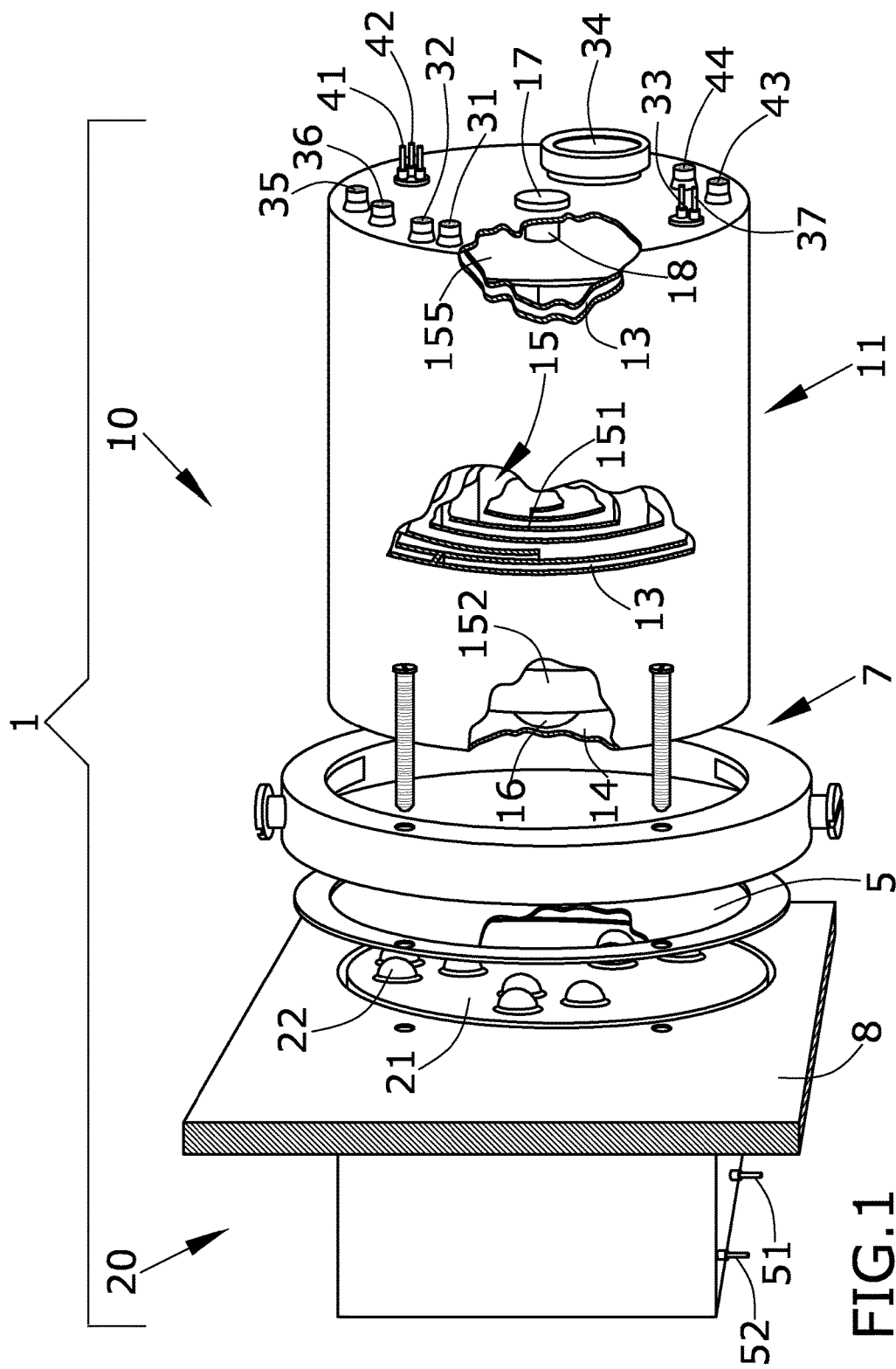
FIG. 1 Represents a first embodiment of the invention, with container comprising a transversal membrane and idle spherical elements as first and second protrusions.

Preferred embodiments of the present invention will now be described with reference to the attached figures, in which the same reference numerals are used to denote the same or corresponding part throughout the several figures.

FIG. 1 shows a cell culture system (1) according to the invention. This system (1) comprises a bottle (10) and a machine (20). In this particular embodiment, both devices are placed on opposite sides of a perforated wall (8) that separates the chambers where the bottle (10) and the machine (20) are placed. An isolating membrane (5) separates the bottle (10) from the machine (20) effectively segregating both sides of the wall (8) and preventing any contact between the bottle (10) and the machine (20).

In another embodiment, each isolated chamber is the size of a room. The wall (8) and the isolating membrane (5) separate two different rooms, thus fully isolating the machine (20) and personnel working on the machine (20) from the bottle (10) and personnel working on the bottle (10). Advantageously, the working space where cells are manipulated is fully isolated from other working spaces with high contamination risk.

In the example of FIG. 1, the bottle (10) is a container (11) comprising the following elements:
- a container membrane (14) placed instead of the base wall of the container (11),
- main movable stirring means (15), comprising a plate (151) and a driven structure (152),
- a guiding housing (17), and
- inlet and outlet connections (35, 36) allowing the supply and extraction of the fluid (4), shown in FIG. 3B, to and from the container (11).

The container membrane (14) closes the container (11) hermetically, so that the container can stay watertight and sterile indefinitely, unless it is opened or broken by other reasons. At the same time, it allows the elements inside the container (11) be affected by the elements outside the container (11) which interact with said container membrane (14).

The plate (151) is a thin sheet, or a set of them, arranged in many different ways in different embodiments, as far as it stirs the fluid (4) contained inside the container (11). Thus, in one embodiment, the plate (151) is a set of helical blades; in another embodiment, the plate (151) is a rolled sheet; in another embodiment, the plate (151) is a set of mill blades; in another embodiment the plate (151) is a set of radial curved blades.

The guiding housing (17) of the container (11) is suitable to house a corresponding guided projection (18) comprised in the main movable stirring means (15), allowing a guided movement of the main movable stirring means (15) in respect of the container (11).

The driven structure (152) is a piece which supports the plate (151) and comprises first protrusions (16). Advantageously, these first protrusions (16) allow the interaction of the bottle (10) with the rest of the elements of the system (1), as it will be described below. In the embodiment shown in this FIG. 1, these first protrusions (16) are idle spherical protrusions.

The machine (20), in turn, comprises impulsion means (21). These impulsion means (21) comprise second protrusions (22). In the embodiment shown in this FIG. 1, these second protrusions (22) are arranged in groups of three semispherical protrusions.

In the embodiment shown in this FIG. 1, the second protrusions (22) are arranged so that each group of three second protrusions (22) house one first protrusion (16). Thus, when this system (1) is operating, the rotating movement of the impulsion means (21) in the machine (20) makes the second protrusions (22) follow a circular trajectory. This circular trajectory is conveyed to the first protrusions (16) of the driven structure (152) via the mechanical coupling between them. This coupling is made possible by the deformations of the isolating membrane (5) and the container membrane (14).

Figure 2B:
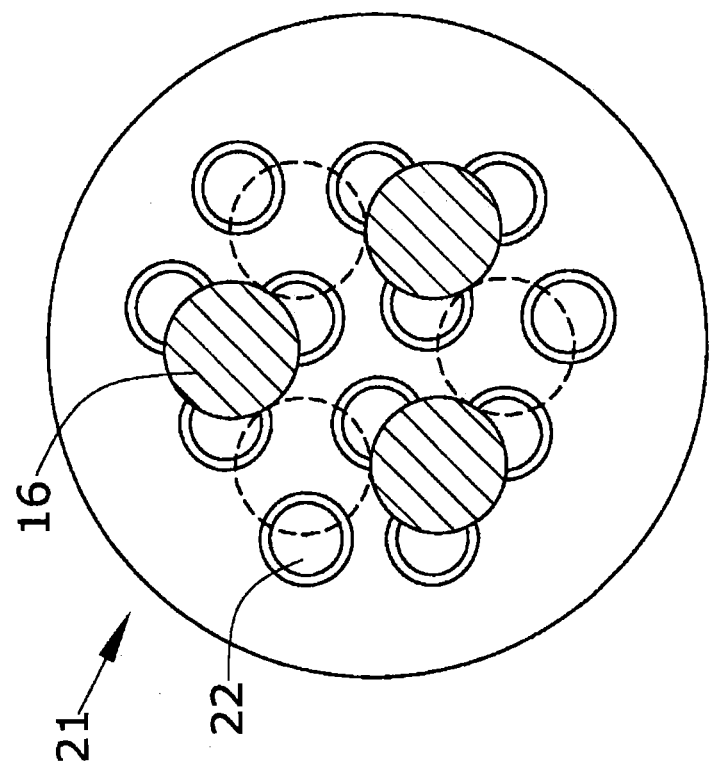
FIGS. 2A-2B Represent details of the interaction between first protrusions and second protrusions in an embodiment of the invention.
Figure 2A:
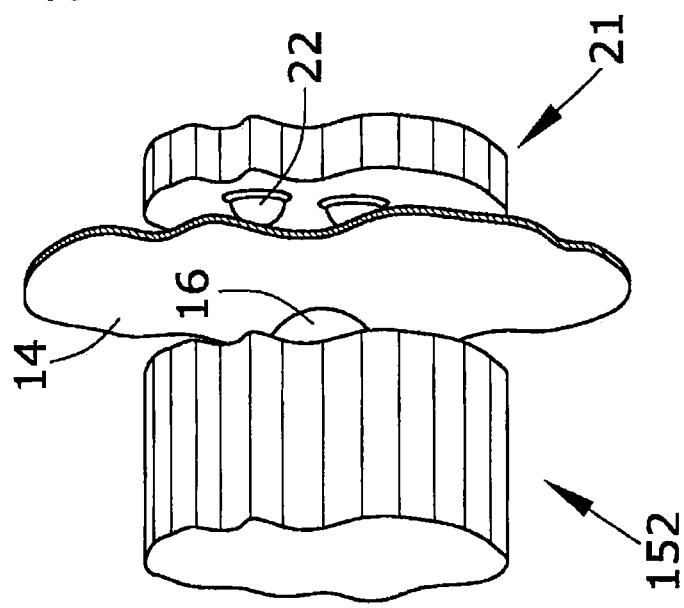

FIG. 2A shows a detail of the interaction between one of the first protrusions (16) and one group of the second protrusions (22), with the intercalating membrane (14) between them.

FIG. 2B shows one particular embodiment of arrangement of the second protrusions (22). In order to ease the correct positioning of the first protrusions (16) relative to the second protrusions (22), said second protrusions (22) are arranged in three groups of three second protrusions (22), located in the vertices of three first equilateral triangles, plus three extra second protrusions (22) arranged to complete three second equilateral triangles with one vertex of two different first equilateral triangles. Advantageously, the first protrusions (16) can be housed in the second protrusions (22) in six different ways that result in equivalent couplings, ensuring that a proper coupling will occur between first and second protrusions while operating the system (1).

Back to FIG. 1, in the embodiment shown in this figure, there are also fastening means (7) that fasten the bottle (10) and the isolating membrane (5) to the wall (8) that separates the chambers where the bottle (10) and the machine (20) are placed.

Advantageously, holding the bottle (10) by one end leaves the bottle overhanging and allows for easy manipulation and placement of tubing and connections.

When the system (1) is in operation, the movement of the impulsion means (21) makes the driven structure (152) and the plate (151) comprised in the main movable stirring means (15) rotate. A constant trajectory for the rotating movement of the driven structure (152) is ensured by the guiding housing (17) that supports the guided projection (18) comprised in the main movable stirring means (15). In this preferred embodiment, both guiding housing (17) and guided projection (18) are concentric to the circular trajectory followed by the impulsion means (21).

The rotating movement of the driven structure (152) is carried out when the impulsion means (21) of the machine (20) is performing a rotating movement. The rotating movement of the impulsion means (21) of the machine (20) makes the plate (151) rotate in the counter clockwise direction thus introducing the fluid (4) inside the plate (151).

FIG. 3A and FIG. 3B show a detail of the interaction between the plate (151), the fluid (4) and the container (11). As it is shown in this FIG. 3A, the gravity makes the fluid (4) accumulate at the bottom of the container (11) and in different zones of the plate (151). In the embodiment shown in this figure, the fluid (4) accumulates at the bottom of the container (11) and at the lower portion of each of the turns of the spiral section of the plate (151), thus allowing for the soaking of the whole spiral plate (151) as it rotates. FIG. 3B shows a side sectional view of the container (11), with the spiral plate (151) and the fluid (4). As it is shown, in this embodiment, the plate (151) is closed in both ends by two lateral walls (155). In this embodiment, one of the walls (155) has a drain hole (153) in communication with the internal cavity of the container (11) to allow outlet of the fluid (4) from the inner part of the spiral sheet such that, in an operative mode, the plate (151) is adapted to transport by rotation the fluid of the container to the inner part of the plate (151), and the drain hole (153) is adapted to return the fluid (4) from the inner part of the plate (151) back to be In contact with the inner walls of the container (11).

Advantageously, this way of conveying the fluid (4) allows for the plate (151) to be in alternating contact both with the fluid (4) and with the gas phase, since the outer end of the open spiral section of the plate (151) does not remain continuously submerged in said fluid (4).

In a particular embodiment, the rotating direction of the impulsion means (21) is reversible. As it was said before, the straight rotating direction of the impulsion means (21) leads to the emptying of the spiral through the drain hole (153) which is in communication with the internal cavity of the container (11). In turn, the inverse rotating direction of the impulsion means (21) leads to the emptying of the spiral through the outer loop of the spiral sheet. The rotation speed and direction of the impulsion means (21) is controlled by a programmable control loop that responds to the value of the parameters measured by probes (41, 42, 33, 37, 51, 52) located both in the container (11) and in the impulsion means (21).

Operation of the system (1) is initiated by fastening the bottle (10) with the fastening means (7) in one of the available positions of the first protrusions (16) and the second protrusions (22).

Then, a thermostating fluid is introduced into the thermostating element (13) through the thermostating fluid inlet (31). In this preferred embodiment the thermostating element (13) is an annular cylindrical chamber surrounding the cylindrical wall of the container (11) where a thermostating fluid at controlled temperature circulates continuously. The thermostating fluid leaves the thermostating element (13) through the thermostating fluid outlet (32). A temperature probe (41) indicates the actual temperature within the container (11) so that flow speed or temperature of the thermostating fluid can be modified in order to reach a set value. In a particular embodiment, this thermostating process is automated by connecting the temperature probe (41) to a sensing element and a control loop with integrated pumps of the type found in the state of art. In another embodiment, the thermostating element (13) is replaced with a surrounding heating wire uniformly distributed on the surface of the device. When this preferred embodiment is used to culture adherent cells, at this point a cell suspension is introduced into the chamber manually through the opening revealed by unscrewing the filter lid (34) or automatically through tubing connected to the fluid supply (44).

Reducing the distance between contiguous loops in the spiral or increasing the volume of the cell suspension leads to the contact of both sides of every loop with the cell suspension, thus increasing the effective area available for cell attachment and subsequent growth.

When the cells contained in the cell suspension coat the surface of the plate (151), fresh culture medium is supplied through the fluid supply (44) while exhausted medium is withdrawn through the fluid drain (43). Automatic feeding with fresh culture medium continues until cell density reaches a defined value. Temperature and pH of the culture medium is controlled with medium temperature probe (33) and medium pH probe (37), respectively. In different embodiments, more parameters such as glucose or dissolved oxygen can be measured by addition of specialized probes. Should the cell culture require the use of a minimum percentage of gaseous carbon dioxide or any other that suits the application, this gas is supplied through gas supply (36) while the excess of gas exits the container (11) through gas drain (35). By use of gas probe (42), the percentage of gaseous carbon dioxide is controlled, thus allowing for adjustment of the flow of gas supply. In another embodiment, the system is placed within a controlled environment where gaseous carbon dioxide is present, so the gas can diffuse into the container (11) through a filtering membrane in the filter lid (34). When the cell culture stage is over and harvesting is to be initiated, the fluid flow through fluid supply (44) switches to a harvesting fluid, such as a trypsin solution, and the harvested cell suspension is recovered through fluid drain (43).

In other embodiment, a washing step with a mild buffered solution is performed before harvesting and/or cell suspension collection happens through the filter lid (34) opening. In another embodiment, rotation speed and direction throughout the entire process is programmably controlled. Further probes (51, 52) on the machine (20) are available for temperature control and impulsion means (21) speed control. In another embodiment, the wall (8) is part of a cover that surrounds the machine (20). In another embodiment, programming, controlling and/or monitoring are carried out from remote locations.

Figure 4:
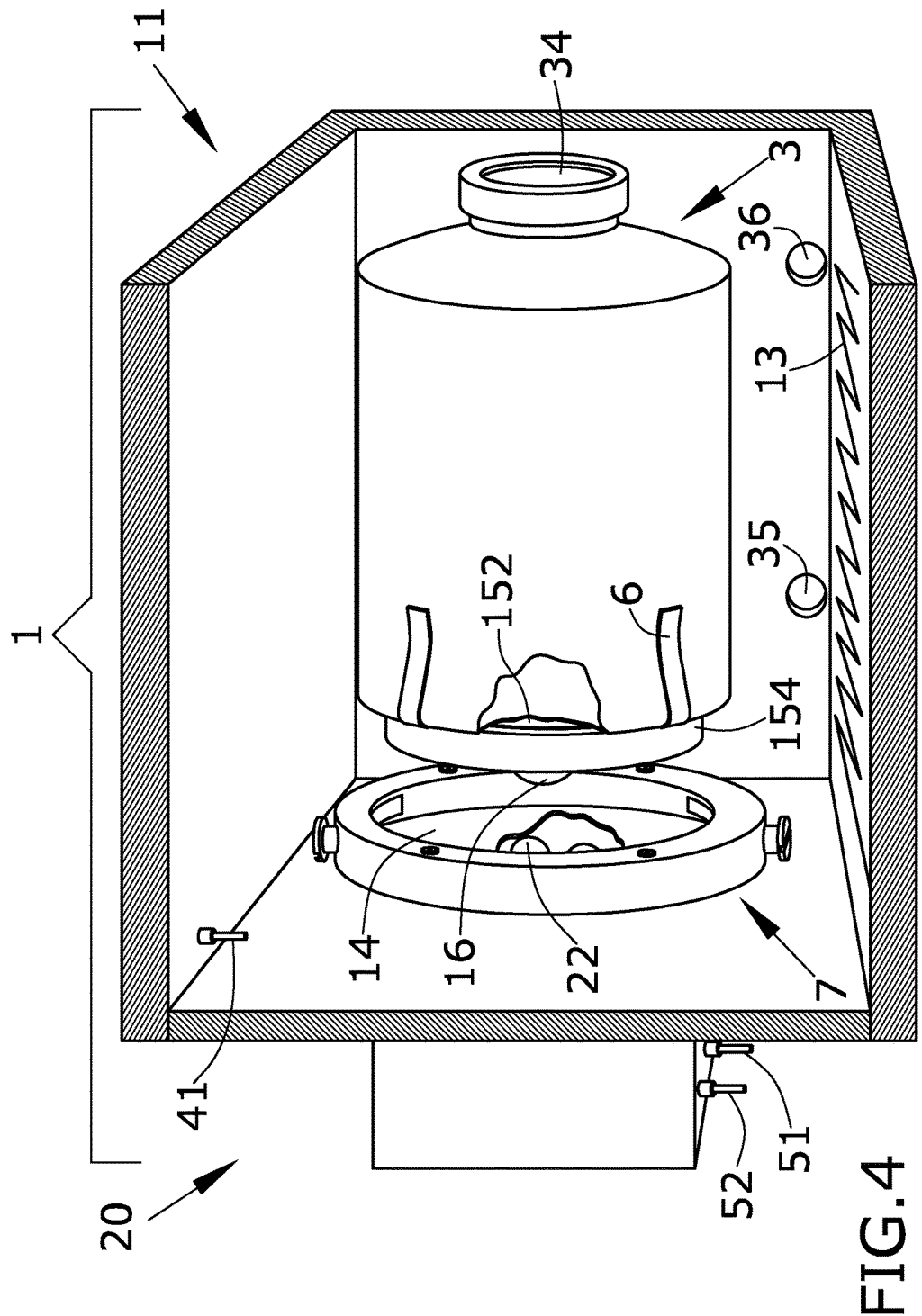
FIG. 4 Represents an embodiment of the invention, with a container comprising a roller bottle.

In a second preferred embodiment, as illustrated in FIG. 4, the container (11) is a thermostated chamber comprising a roller bottle (3) inside, and the machine (20) is the same as in the embodiment of FIG. 1. The machine (20), thus, comprises impulsion means (21), which, in turn, comprise second protrusions (22). In the embodiment shown in this FIG. 4, these second protrusions (22) are arranged in groups of three idle spherical protrusions and the thermostating element (13) is a heated wire.

In the embodiment shown in this FIG. 4, the second protrusions (22) are arranged in the same way as in the embodiment of FIG. 1.

The roller bottle (3) of this embodiment comprises the fluid (4) inside. The roller bottle (3) also comprises the driven structure (152) and the driven structure (152) comprises a rotatable annulus (154) and the first protrusions (16), which interact with the second protrusions (22).

In a particular embodiment, the roller bottle (3) comprises securing means, such as clamps (6). In this figure, the roller bottle (3) is secured by a set of clamps (6), allowing for easy removal and replacement.

In the embodiment shown in this FIG. 4, there are also fastening means (7) that fasten the annulus (154) and the container membrane (14) to the wall (8).

In this second embodiment, the container membrane (14) segregates the machine (20) from the inner part of the container (11) where the roller bottle (3) is located.

When this second preferred embodiment is used In cell culture processes, removal and replacing of the roller bottle (3) can be performed manually during operation, since rotating speed used in this processes is usually slower than 5 rpm. When the machine (20) operates, it sets the driving structure (152) in motion and, as described for the first preferred embodiment, the rotating movement will be conveyed to the roller bottle (3), which is horizontally placed. Advantageously, when this rotational movement occurs, the culture media continuously soaks the Inner side of the cylindrical wall of the roller bottle (3) where adherent cells are attached, thus feeding the cells. In other embodiment, several systems (1) are arranged in the same wall (8) with different container membranes (14) forming a multi-chamber machine. In other embodiment, several roller bottles (3) are installed within a large single container (11), advantageously multiplying the throughput of the overall system.

Figure 5:
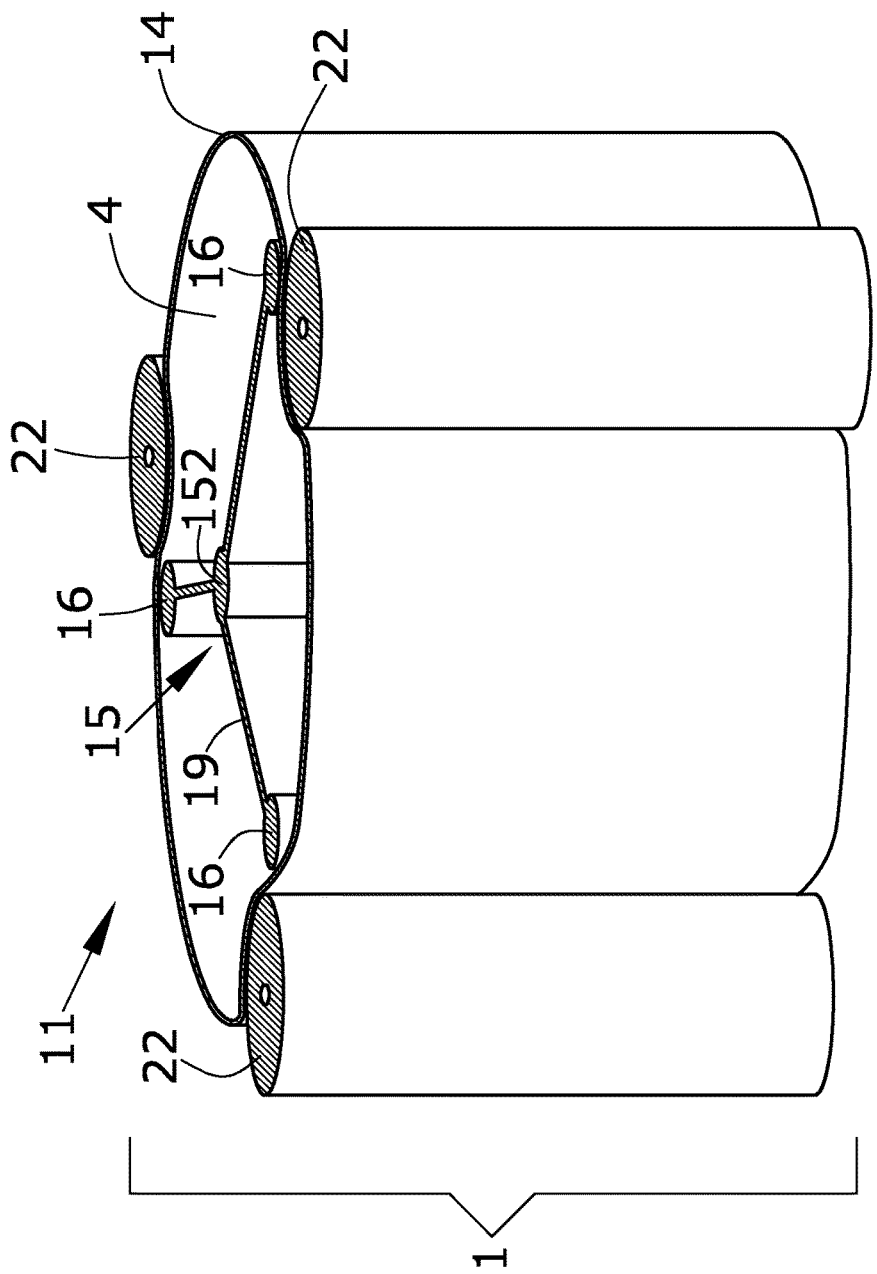
FIG. 5 Shows a cut section of a third preferred embodiment of the invention, with cylindrical first and second protrusions and a peripheral membrane in the container.

A third preferred embodiment is partially represented in FIG. 5. As shown in the figure, three cylindrical second protrusions (22) are arranged parallel to the longitudinal axis of the cylindrical container membrane (14). Since the distance from each second protrusion (22) to the center of the container membrane (14) is shorter than the radius of the container membrane (14), a deformation of the container membrane (14) is created by each of the second protrusions (22). In the embodiment shown in this figure, first protrusions (16) are, in turn, three cylindrical first protrusions, parallel to the cylindrical second protrusions (22). They are all linked with the driven structure (152), by a series of connecting elements (19) that join the center element with each cylindrical first protrusion (16).

When the second protrusions (22) rotate, they follow a circular trajectory concentric to the container (11) axis while simultaneously rolling on the container membrane (14) and thus rotating about their respective longitudinal axis. The combined effect of the moving second protrusions (22) and the pressure within the container (11) due to the fluid contained in the container (11) makes the deformations in the flexible container membrane (14) follow a circular trajectory corresponding to the trajectory followed by the second protrusions (22). When the resulting deformations created in the container membrane (14) encounter the first protrusions (16) the driven structure (152) is forced to rotate following a trajectory concentric to the container (11) axis, therefore making the connecting elements (19) linking the cylindrical first protrusions (16) to the driven structure (152) agitate the fluid (4) within the container (11).

Advantageously, the first inter-related product disclosed in the present invention can be fully built in materials, such as plastic, adequate for radiation sterilization, such as gamma radiation.

Advantageously, these embodiments offer a major improvement of watertightness, containment and sterility of the container (11) contents, without affecting the internal working of the main movable stirring means (15). This is so even though, these main movable stirring means (15) perform a better working, being even more suitable than the current devices for several biotechnological applications, such as:
  stirring and mixing of fluids in chemistry industry,
  pumping of fluids,
  production of cells, nucleic acids, proteins and other biopharmaceuticals,
  production of living tissues, especially artificial skin,
  modification of fluid composition, by the action of some elements affixed in the plate, e.g., enzymatic modifications or alike processes,
  the use of the system for the breeding of water organisms.

The invention claimed is:

1. A first inter-related product for non intrusive agitation of a fluid, suitable for cell culture, provided in the form of a device comprising:
   a container to contain directly or by a further second container the fluid, the container comprising an inner part, an outer part and walls, at least one of the walls comprising a first flexible element having an internal surface oriented towards the inner part of the container and an external surface oriented towards the outer part of the container,
   main movable stirring means located inside the container to stir at least the fluid,
   wherein,
   the external surface of the first flexible element is to interfere mechanically with an external movable impulsion means thus creating a deformation on the internal surface of the first flexible element such that said deformation of the internal surface of the first flexible element has a mechanical interference with the main movable stirring means, and movement of such impulsion means is transmitted to the main movable stirring means by interposition of the first flexible element,
   wherein the main movable stirring means comprises first protrusions, and at least one of the first protrusions are cylindrical protrusions, semicylindrical protrusions, semispherical protrusions, idle cylinders, idle spherical elements, retractile bars, or a combination thereof.

2. The first inter-related product according to claim 1, wherein the main movable stirring means are mechanically coupled to a secondary stirring means located within the container wherein movement of the secondary stirring means is driven by movement of the main movable stirring means.

3. The first inter-related product according to claim 1, wherein a surface of the main movable stirring means is modified by means of functionalising said surface or coating said surface with catalysts, chemical reagents, cells, polymers, or crystals.

4. The first inter-related product according to claim 1, further comprising inlet and outlet means to supply and extract at least one fluid from the container.

5. The first inter-related product according to claim 1, wherein the container comprises a guiding housing and the main movable stirring means comprises at least one corresponding guided projection to be housed in the guiding housing of the container allowing a guided movement of the main movable stirring means with respect to the container.

6. The first inter-related product according to claim 1, wherein the container comprises a temperature control means to keep a constant temperature within the container.

7. The first inter-related product according to claim 1, wherein:
the container is a cylindrical wall extended according to a longitudinal axis and limited by two ends wherein at least one end is a transversal wall comprising the first flexible element,
the container is to be oriented such that the longitudinal axis is essentially perpendicular to the direction of gravity, and
the main movable stirring means comprises a plate and a driven structure attached thereto, where the first protrusions are located, to interact with the deformation of the internal surface of the first flexible element.

8. The first inter-related product according to claim 7, wherein the plate comprises a spiral section and extends along the longitudinal axis of the container between a first end and a second end.

9. The first inter-related product according to claim 8, wherein the plate comprising the spiral section is closed in both ends by two lateral walls, at least one of the walls having a drain hole in communication with an internal cavity of the container for allowing an outlet of the fluid from an inner part of the plate comprising the spiral section such that, in an operative mode, the plate comprising the spiral section is to transport by rotation the fluid of the container to the inner part of the plate having the spiral section, and the drain hole is to return the fluid from the inner part of the plate to an outer part of the plate back to be in contact with inner walls of the container.

10. The first inter-related product according to claim 9, wherein the main movable stirring means comprises a set of nested cylinders such that:
each cylinder is in fluid connection with the cylinder immediately housing it,
the drain hole of the plate comprising the spiral section is in fluid communication with the most inner cylinder, and
the outermost cylinder is in fluid communication with the container;
such that the outlet of the fluid from the inner part of the plate comprising the spiral section to the container is by the interposition of the set of nested cylinders.

11. The first inter-related product according to claim 10, wherein the fluid connection of each cylinder with the cylinder immediately housing it is by means of outlets located in alternating ends in such a way the flow is alternating the direction when flowing in each cylinder.

12. The first inter-related product according to claim 1, wherein:
the container is a cylindrical wall extended according to a longitudinal axis and limited by two ends wherein the cylindrical wall comprises the first flexible element,
the container is to be oriented such that the longitudinal axis is essentially parallel to the direction of gravity, and
the main movable stirring means comprises a driven structure attached thereto, where the first protrusions are located, to interact with the deformation of the internal surface of the first flexible element.

13. The first inter-related product according to claim 12, wherein the first protrusions are cylindrical first protrusions substantially parallel to the longitudinal axis of the container and linked with the driven structure by connecting elements.

14. The first inter-related product according to claim 12, wherein the main movable stirring means further comprises a plate comprising a helical portion or helical blades with its longitudinal axis essentially parallel to the longitudinal axis of the container and to raise the fluid contained in the container.

15. The first inter-related product according to claim 1, wherein the container comprises a second container to store said fluid and the second container is integral with the main movable stirring means.

16. The first inter-related product according to claim 1, wherein the first flexible element is a membrane.

17. A system comprising a combination of the first inter-related product according to claim 1 and a second inter-related product provided in the form of impulsion means adapted to act over the surface of a flexible element, particularly the external surface of the first flexible element of the first inter-related product and intended to be located outside the container of such first inter-related product, wherein said impulsion means comprises at least one second protrusion adapted to interfere mechanically with the external surface of the flexible element causing the deformation of said flexible element protruding the internal surface.

18. The system according to claim 17, wherein the movement direction of the impulsion means is reversible.

19. The system according to claim 17, wherein the movement of the impulsion means is lineal circular or a combination of both.

20. The system according to claim 17, further comprising a plurality of second protrusions, wherein the impulsion means and the main movable stirring means are arranged so that the arrangement of the second protrusions provides corresponding housings for the first protrusions by the interposition of the first flexible element.

21. The system according to claim 20, wherein the second protrusions are adapted to provide corresponding housings for the first protrusions in more than one housing position.

22. The system according to claim 17, wherein at least one of the second protrusions are cylindrical protrusions, semi-cylindrical protrusions, semispherical protrusions, idle cylinders, idle spherical elements, or a combination thereof.

23. The system according to claim 17, wherein the second protrusions are one or more cylinders parallel to the longitudinal axis of the container.

24. The system according to claim 23, wherein the first flexible element surrounds the longitudinal axis of the container and the second protrusions are adapted to be rotatable around the longitudinal axis of the container.

25. The system according to claim 17, wherein the first inter-related product is located in a first chamber and the second inter-related product is located in a second chamber, said chambers separated by a wall, the wall further comprising a second flexible element located between the impulsion means and the first flexible element of the container.

* * * * *